United States Patent
Mendrok-Edinger et al.

(10) Patent No.: US 9,980,889 B2
(45) Date of Patent: May 29, 2018

(54) COMPOSITIONS COMPRISING P-HYDROXYBENZYLAMINE

(71) Applicant: DSM IP ASSETS B.V., Heerlen (NL)

(72) Inventors: Christine Mendrok-Edinger, Basel (CH); Rainer Voegeli, Basel (CH); Peter Wikstroem, Basel (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days. days.

(21) Appl. No.: 15/331,711

(22) Filed: Oct. 21, 2016

(65) Prior Publication Data
US 2017/0035668 A1 Feb. 9, 2017

Related U.S. Application Data

(62) Division of application No. 14/420,807, filed as application No. PCT/EP2013/066824 on Aug. 12, 2013, now abandoned.

(30) Foreign Application Priority Data

Sep. 3, 2012 (EP) .................................... 12182760

(51) Int. Cl.
| | | |
|---|---|---|
| *A01N 33/04* | (2006.01) | |
| *A01N 33/24* | (2006.01) | |
| *A61K 8/41* | (2006.01) | |
| *A61K 8/89* | (2006.01) | |
| *A61Q 5/02* | (2006.01) | |
| *A61Q 5/12* | (2006.01) | |
| *A61Q 19/00* | (2006.01) | |
| *A61Q 17/00* | (2006.01) | |
| *A61K 8/04* | (2006.01) | |
| *A61K 8/06* | (2006.01) | |
| *A61Q 1/02* | (2006.01) | |
| *A61Q 5/00* | (2006.01) | |
| *A61Q 19/10* | (2006.01) | |

(52) U.S. Cl.
CPC ............. *A61K 8/41* (2013.01); *A01N 33/04* (2013.01); *A01N 33/24* (2013.01); *A61K 8/042* (2013.01); *A61K 8/062* (2013.01); *A61K 8/064* (2013.01); *A61K 8/89* (2013.01); *A61Q 1/02* (2013.01); *A61Q 5/006* (2013.01); *A61Q 5/02* (2013.01); *A61Q 5/12* (2013.01); *A61Q 17/005* (2013.01); *A61Q 19/00* (2013.01); *A61Q 19/007* (2013.01); *A61Q 19/10* (2013.01); *A61K 2800/52* (2013.01); *A61K 2800/74* (2013.01)

(58) Field of Classification Search
CPC .............................. A01N 33/04; A01N 33/24
See application file for complete search history.

(56) References Cited

U.S. PATENT DOCUMENTS

| | | |
|---|---|---|
| 3,726,969 A | 4/1973 | Johnson et al. |
| 2015/0374737 A1 | 12/2015 | Lin |

FOREIGN PATENT DOCUMENTS

| | | |
|---|---|---|
| RU | 2240772 C1 * | 11/2004 |
| WO | 2012064340 | 5/2012 |

OTHER PUBLICATIONS

International Search Report for PCT/EP2013/066824 dated Sep. 24, 2013, 5 pages.
J. C. Slaughter et al., "The Identification of p-hydroxybenzylamine in Barley and Malt", Phytochemistry, vol. 11, No. 1, Jan. 1, 1972, pp. 478-479.
M. Koyama et al., "Identification of Hydroxybenzylamines in Buckwheat Seeds (Fagopyrum Esculentum Moench)", Agr. Biol. Chem., Jan. 1, 1971, pp. 1870-1879.
M. Houslay et al., "A Kinetic Evaluation of Monoamine Oxidase Activity in Rat Liver Mitochondrial Outer Membranes", Biochem. J., Jan. 1, 1974, pp. 645-652.
Y. H. Tao et al., "Inhibition of Gaba Shunt Enzymes' Activity by 4-hydroxybenzaldehyde Derivatives", Bioorganic & Medicinal Chemistry Letters, vol. 16, No. 3, Feb. 1, 2006, pp. 592-595.
L. Xingliang et al., "Inactivation of Mitochondrial Monomine Oxidase B by Methylthio-Substituted Benzylamines", Bioorganic & Medicinal Chemistry, vol. 11, No. 20, Oct. 1, 2003, pp. 4423-4430.
D. Alesiani et al., "Antioxidant and Antiproliferative Activities of Photochemicals from Quince (*Cydonia vulgaris*) Peels", Food Chemistry, vol. 118, No. 2, Jan. 15, 2010, pp. 199-207.
D. Santi et al., "Tyrosyl Transfer Ribonucleic Acid Synthetase from *Escherichia coli* B, Analysis of Tyrosine and Adenosine 5'-Triphosphate Binding Sites", Journal of Medicinal Chemistry, Mar. 1, 1973, pp. 273-280.
W. Siegert, "ISO 11930—A Comparison to other Methods to Evaluate the Efficacy of Antimicrobial Preservation," SOFW—Journal, 138, English Edition, International Journal for Applied Science, pp. 44-53, Jul. 2012.

* cited by examiner

*Primary Examiner* — Gina C Justice
(74) *Attorney, Agent, or Firm* — Nixon & Vanderhye P.C.

(57) ABSTRACT

The present invention relates to the use of p-hydroxybenzylamine or a salt thereof as antimicrobial agent as well as to composition comprising said agent.

6 Claims, No Drawings

COMPOSITIONS COMPRISING P-HYDROXYBENZYLAMINE

This application is a divisional of commonly owned U.S. Ser. No. 14/420,807, filed Feb. 10, 2015, (now abandoned), which is the national phase application of international application PCT/EP2013/066824, filed Aug. 12, 2013, which designated the US and claims priority to European Patent Application 12182760.4, filed Sep. 3, 2012, the entire contents of each of which are hereby incorporated by reference.

The present invention relates to the use of p-hydroxybenzylamine or a salt thereof as antimicrobial agent as well as to composition comprising said agent.

To protect cosmetics against mold and bacteria, most cosmetic products currently on the market contain preservatives. While these preservatives protect against bacteria and fungi, studies have linked daily exposure to many of these substances to an increased risk of skin irritation, cancer and/or endocrine problems. Thus, many cosmetic manufactures are searching for alternatives which don't appear to pose any health risks.

Surprisingly, it has been found that p-hydroxybenzylamine exhibits an antimicrobial activity.

Thus, the present invention relates to the use of p-hydroxybenzylamine or a salt thereof as antimicrobial agent, i.e. an agent which exhibits an antimicrobial activity. In particular the present invention is directed to the use of p-hydroxybenzylamine or a salt thereof as anti-fungal and/or anti-bacterial agent, more in particular as an agent for inhibiting the growth of *Escherichia coli* (*E. coli*), *Pseudomonas aeruginosa* (*P. aeruginosa*), *Staphylococcus aureus* (*S. aureus*), *Propionibacterium acnes* (*P. acnes*), *Aspergillus brasiliensis* (*A. brasiliensis*) and/or *Candida albicans* (*C. albicans*).

In another embodiment, the invention relates to a method for killing and/or inhibiting growth of microbial cells, in particular fungal and/or bacterial cells, said method comprising contacting said microbial cells with p-hydroxybenzylamine or a salt thereof. In a preferred embodiment the microbial cells are selected from the group consisting of *E. coli, P. aeruginosa, S. aureus, P. acnes, A. brasiliensis* and *C. albicans* as well as mixtures thereof.

In another embodiment the invention relates to a method of preventing microbial decay and breakdown of cosmetic compositions, said method encompassing the addition of 0.001 to 10 wt.-% of p-hydroxylbenzylamine or a salt thereof into said composition. In a particular embodiment the method also encompasses the step of appreciating the result. In another particular embodiment, the cosmetic composition furthermore comprises water and at least one further agent selected from the group consisting of surfactants, emulsifiers, thickeners, and oils. Preferred oils are silicone oils.

The antimicrobial activity of p-hydroxybenzylamine or a salt thereof is in particular suitable for preventing decay and breakdown of cosmetic compositions comprising water and at least one further agent selected from the group consisting of surfactants, emulsifiers, thickeners and oils as such compositions are particular sensitive to microbial growth. Preferred oils are silicone oils.

Thus, in another embodiment, the invention is also directed to cosmetic compositions comprising water and at least one agent selected from the group consisting of surfactants, emulsifiers, thickeners and oils, wherein the composition furthermore comprises p-hydroxylbenzylamine or a salt thereof in an amount of 0.001 to 10 wt.-%, based on the total weight of the composition. Preferably, the oils are silicone oils. In a particular embodiment, the composition is free of any hair dying agent, i.e. is not suitable for dying hair.

In another embodiment, the antimicrobial activity of p-hydroxybenzylamine or a salt thereof can be used for the treatment of dandruff. Thus, the invention also relates to a method of treating the scalp, said method comprising the steps of contacting the scalp with a hair care preparation comprising p-hydroxybenzylamine or a salt thereof, preferably in an amount of 0.001 to 10 wt.-% based on the total weight of the composition. In a preferred embodiment the method is directed to the treatment of dandruff. In another preferred embodiment the hair care preparation is a rinse off composition in the form of a shampoo or a conditioner. In a further preferred embodiment, the method furthermore comprises the step of rinsing the hair with water.

In all embodiments of the present invention p-hydroxylbenzylamine is preferably used in an amount selected in the range of about 0.005 to 5 wt.-%, such as in the range of about 0.01 to 1 wt.-%, based on the total weight of the composition.

The term "antimicrobial activity" (or "antimicrobial effect") as used herein means a capability of killing and/or inhibiting the growth of microbial cells such as in particular bacteria and fungi and more in particular *E. coli, P. aeruginosa, S. aureus, P. acnes, A. brasiliensis* and/or *C. albicans*. p-Hydroxybenzylamine is also known as 4-hydroxybenzylamine respectively 4-(aminomethyl)-phenol [CAS 696-60-6] and is e.g. commercially available at Ugarit Chimie (Issy les Moulineux, France).

According to the present invention p-hydroxybenzylamine can also be employed in the form of a salt thereof. Suitable salts encompass e.g. salts obtainable with acids, such as e.g. with mineral acids such as hydrogen chloride, hydrogen bromide, sulphuric acid or phosphoric acid; with appropriate carboxylic acids, e.g. aliphatic mono- or dicarboxylic acids such as formic acid, acetic acid, trifluoroacetic acid, trichloroacetic acid, propionic acid, glycolic acid, succinic acid, fumaric acid, malonic acid, maleic acid, oxalic acid, phthalic acid, citric acid, lactic acid or tartaric acid; with aromatic carboxylic acids such as benzoic acid or salicylic acid; with aromatic-aliphatic carboxylic acids such as mandelic acid or cinnamic acid; with heteroaromatic carboxylic acids such as nicotinic acid; or with aliphatic or aromatic sulfonic acids such as methanesulfonic acid or toluenesulfonic acid. Particular suitable salts of p-hydroxybenzylamine for the purpose of the present invention are the hydrochloride [CAS 1004-23-5] or the hydrobromide [CAS 90430-14-1].

Preferably, in all embodiments of the present invention p-hydroxybenzylamine is used in the form of its hydrochloride. Nevertheless, even if incorporated as free amine, the actual form of p-hydroxybenzylamine in the compositions according to the present invention, i.e. its existence as free amine or a salt thereof may depend on the respective pH/mixture of a specific composition.

The cosmetic compositions according to the present invention are in particular topically applied to mammalian keratinous tissue such as in particular to human skin or the human scalp and hair.

The term "cosmetic composition" as used in the present application refers to cosmetic compositions as defined under the heading "Kosmetika" in Römpp Lexikon Chemie, 10th edition 1997, Georg Thieme Verlag Stuttgart, New York as well as to cosmetic compositions as disclosed in A. Domsch, "Cosmetic Compositions", Verlag für chemische Industrie (ed. H. Ziolkowsky), $4^{th}$ edition, 1992.

Suitable surfactants, emulsifiers, thickeners, and oils—such as preferably silicone oils—for the purpose of the present inventions are ails surfactants, emulsifiers, thickeners, and oils commonly used in cosmetic applications and which are e.g. listed in CTFA Cosmetic Ingredient Handbook, First edition 1988. Such suitable surfactants, emulsifiers, thickeners, and oils are well known to a person skilled in the art.

The cosmetic compositions according to the present invention preferably further comprise a physiologically acceptable medium, that is to say a medium compatible with keratinous substances, such as the skin, mucosa, and keratinous fibres. In particular the physiologically acceptable medium is a cosmetically acceptable carrier.

The term cosmetically acceptable carrier refers to all carriers and/or excipients and/or diluents conventionally used in cosmetic compositions.

Preferably, the cosmetic compositions according to the invention are in the form of a suspension or dispersion in solvents or fatty substances, or alternatively in the form of an emulsion or micro emulsion (in particular of O/W- or W/O-type), PIT-emulsion, nano emulsion, multiple emulsion (e. g. O/W/O- or W/O/W-type), pickering emulsion, hydrogel, lipogel, one- or multiphase solution or vesicular dispersion.

The cosmetic compositions in accordance with the invention can be in the form of a liquid, lotion, a thickened lotion, a gel, a cream, a milk, an ointment or a paste.

The cosmetic compositions according to the invention have a pH in the range of 3-10, preferably in the range of pH of 4-8, most preferred in the range of pH 5-7. The pH is adjusted by methods known to a person skilled in the art, e.g. by using an acid such as a hydroxy acid including glycolic acid, lactic acid, malic acid, citric acid and tartaric acid or a base such as e.g. sodium or potassium hydroxide or ammonium hydroxide as well as mixtures thereof.

Preferably, in the compositions according to the invention citric acid in an amount of at least 0.0001 wt.-%, such as e.g. in an amount of 0.01-1 wt.-%, in particular in an amount of 0.01 to 0.5 wt.-% is used for pH adjustment.

The cosmetic compositions according to the present invention are in particular skin care preparations, functional preparations and/or hair care preparations such as most in particularly skin or hair care preparations.

Examples of skin care preparations are, in particular, light protective preparations, anti-ageing preparations, preparations for the treatment of photo-ageing, body oils, body lotions, body gels, treatment creams, skin protection ointments, moisturizing preparations such as moisturizing gels or moisturizing sprays, face and/or body moisturizers, skin-tanning preparations (i.e. compositions for the artificial/sunless tanning and/or browning of human skin), for example self-tanning creams as well as skin lightening preparations.

Examples of functional preparations are cosmetic compositions containing active ingredients such as hormone preparations, vitamin preparations, vegetable extract preparations, anti-ageing preparations, and/or antimicrobial (antibacterial or antifungal) preparations without being limited thereto.

Examples hair care preparations which are suitable according to the invention and which may be mentioned are shampoos, hair conditioners (also referred to as hair rinses), hairdressing compositions, hair tonics, hair regenerating compositions, hair lotions, water wave lotions, hair sprays, hair creams, hair gels, hair oils, hair pomades or hair brilliantines. Accordingly, these are always preparations which are applied to the hair and the scalp for a shorter or longer time depending on the actual purpose for which they are used.

In a particular preferred embodiment of the invention the hair care preparations are used for the treatment of dandruff. The addition of p-hydroxybenzylamine or a salt thereof to hair care preparations effects simultaneous dandruff treatment. However, it is also possible to produce preparations which are used primarily or exclusively for the purpose of reducing and/or eliminating dandruff.

If the hair care preparations according to the invention are supplied as shampoos, these can be clear liquids, opaque liquids (with pearly luster effect), in cream form, gel-like or else in powder form or in tablet form, and as aerosols. The surfactant raw materials on which these shampoos are based can be anionic, cationic, nonionic and amphoteric in nature and also be present in combinations of these substances.

Examples of anionic surfactants suitable for the incorporation into the shampoo preparations according to the present invention are $C_{10-20}$ alkyl- and alkylenecarboxylates, alkyl ether carboxylates, fatty alcohol sulfates, fatty alcohol ether sulfates, alkylolamide sulfates and sulfonates, fatty acid alkylolamide polyglycol ether sulfates, alkanesulfonates and hydroxyalkanesulfonates, olefinsulfonates, acyl esters of isothionates, alpha-sulfo fatty acid esters, alkylbenzenesulfonates, alkylphenol glycol ether sulfonates, sulfosuccinates, sulfosuccinic monoesters and diesters, fatty alcohol ether phosphates, protein-fatty acid condensation products, alkyl monoglyceride sulfates and sulfonates, alkyl glyceride ether sulfonates, fatty acid methyltaurides, fatty acid sarcosinates, and sulforicinoleates. These compounds and their mixtures are used in the form of their salts which are soluble in water or dispersible in water, for example the sodium, potassium, magnesium, ammonium, mono-, di- and triethanolammonium and analogous alkylanunonium salts.

Examples of suitable cationic surfactants are quaternary ammonium salts such as di($C_{10}$-$C_{24}$alkyl)dimethylammonium chloride or bromide, preferably di ($C_{12}$-$C_{18}$alkyl)-dimethylammonium chloride or bromide; $C_{10}$-$C_{24}$-alkyldimethylethylammonium chloride or bromide; $C_{10}$-$C_{24}$-alkyltrimethylammonium chloride or bromide, preferably cetyltrimethylammonium chloride or bromide and $C_{20}$-$C_{24}$-alkyltrimethylammonium chloride or bromide; $C_{10}$-$C_{24}$4-alkyldimethylbenzylammonium chloride or bromide, preferably $C_{12}$-$C_{18}$-alkyldimethylbenzylammoniumchloride; N—($C_{12}$-$C_{18}$-alkyl)pyridinium chloride or bromide, preferably N—($C_{12}$-$C_{16}$-alkyl)pyridinium chloride or bromide; N—($C_{12}$-$C_{18}$-alkyl)isoquinolinium chloride, bromide or monoalkyl sulfate; N—($C_{12}$-$C_{18}$-alkyloylcolaminoformylmethyl)pyridinium chloride; N—($C_{12}$-$C_{18}$-alkyl)-N-methylmorpholinium chloride, bromide or monoalkyl sulfate; N—($C_{12}$-$C_{18}$-alkyl)-N-ethylmorpholinium chloride, bromide or monoalkyl sulfate; $C_{16}$-$C_{18}$-alkylpentaoxethylammonium chloride; isobutylphenoxyethoxyethyldimethyl-benzylammonium chloride; salts of N,N-diethylaminoethylstearylamide and oleylamide with hydrochloric acid, acetic acid, lactic acid, citric acid, phosphoric acid; N-acylamidoethyl-N,N-diethyl-N-methylammonium chloride, bromide or monoalkylsulfate and N-acylaminoethyl-N,N-diethyl-N-benzylammonium chloride, bromide or monoalkyl sulfate, where acyl is preferably stearyl or oleyl.

Examples of suitable nonionic surfactants which can be used as detergent substances are fatty alcohol ethoxylates (alkylpolyethylene glycols); alkylphenol polyethylene glycols; alkyl mercaptan polyethylene glycols; fattyamine ethoxylates (alkylaminopolyethylene glycols); fatty acid ethoxylates (acylpolyethylene glycols); polypropylene glycol ethoxylates (Pluronic); fatty acid alkylolamides (fatty acid amide polyethylene glycols); sucrose esters; sorbitol esters and polyglycol ether.

Examples of amphoteric surfactants which can be added to the shampoos are N—($C_{12}$-$C_{18}$-alkyl)-.beta.-aminopropionates and N—($C_{12}$-$C_{18}$-alkyl)-.beta.-iminodipropionates as alkali metal and mono-, di- and trialkylammonium salts; N-acylamidoalkyl-N,N-dimethylacetobetaine, preferably N—($C_5$-$C_{18}$-acyl)amidopropyl-N,N-dimethylacetobetaine; $C_{12}$-$C_{18}$-alkyldimethylsulfopropylbetaine; amphoteric surfactants based on imidazoline (commercial name: Miranol®, Steinapon®), preferably the sodium salt of 1-(β-carboxymethyloxyethyl)-1-(carboxymethyl)-2-laurylimidazolinium; amine oxide, for example $C_{12}$-$C_{18}$-alkyldimethylamine oxide, fatty acid amidoalkyldimethylamine oxide.

The hair care preparations according to the invention can additionally contain further additives customary in hair care such as for example perfumes, colorants, also those which simultaneously dye or tint the hair, solvents, opacifying agents and pearly luster agents, for example esters of fatty acids with polyols, magnesium and zinc salts of fatty acids, dispersions based on copolymers, thickening agents such as sodium, potassium and ammonium chloride, sodium sulfate, fatty acid alkylolamides, cellulose derivatives, natural rubbers, also plant extracts, protein derivatives such as gelatin, collagen hydrolysates, polypeptides with a natural or synthetic basis, egg yolk, lecithin, lanolin and lanolin derivatives, fats, oils, fatty alcohols, silicones, deodorizing agents, substances with antimicrobial activity, substances with antiseborrhoeic activity, substances with keratolytic and keratoplastic effect, such as, for example, sulfur, salicylic acid and enzymes as well as further anti-dandruff agents such as olamine, climbazol, zink pyrithion, ketoconazole, salicylic acid, sulfur, tar preparations, derivatives of undecenic acid, extracts of nettel, rosmary, cottonwood, birch, walnut, willow bark and/or arnica which may act even synergistically with the p-hydroxybenzylamine or a salt thereof in the treatment of dandruff.

For the preparation of the hair care preparations the p-hydroxybenzylamine or a salt thereof is dissolved under stirring at a temperature in the range between 20 and 60° C., preferably at room temperature, in the detergent substance used. Subsequently, the further additives are added.

In the event of alcohol containing scalp respectively hair care preparations p-hydroxybenzylamine or a salt thereof is dissolved in the alcohol at a temperature in the range between 20 and 40° C., preferably at room temperature. Subsequently, the further additives are added. In the event of hair rinses and oil-in-water emulsions the active substance is dissolved in the fatty phase, which means together with the oil and the emulsifier at a temperature in the range between 70 and 90°, preferably at 75° C. Subsequently, hot water is added and the emulsion is stirred and cooled.

The shampoos are produced in a manner known per se by mixing the individual components and where necessary further processing appropriate for the particular type of preparation.

Examples of hair care preparations in which the p-hydroxybenzylamine or a salt thereof can be used according to the invention and which may be mentioned are hair conditioners, hair tonics and hair regenerating compositions, which are rinsed off from the hair after a certain time or, depending on the formulation, can also remain on the hair. These products contain, inter alia, substances from the group of the above mentioned cationic surfactants which display a reviving and antistatic property on the hair.

The hair care preparations according to the invention, in particular for the treatment of dandruff, can also be supplied in the form of aqueous and aqueous alcoholic hair lotions, water wave lotions (hair setting compositions), also those in gel form, and in aerosol form as hair spray, as well as in the form of hair care and hairdressing creams and gels. Ethanol and isopropanol are preferably used as alcohols.

All these preparations are also produced as already mentioned for the shampoo in a manner known per se with the addition of the p-hydroxybenzylamine or a salt thereof.

The p-hydroxybenzylamine or a salt thereof is incorporated in the scalp respectively hair care preparations according to the invention in amounts which are normally between about 0.001 and about 10%. Within this range, the concentrations of the specific preparations depend on the purpose for which they are used. Certain formulations such as, for example, concentrates which must be diluted before they are used may also have considerably higher concentrations.

If the preparations remain on the hair, such as, for example, hair lotions, hair setting compositions, creams, etc., lower concentrations will be used, for example of about 0.01 to about 3%, preferably 0.1 to 2%. They are expediently used in higher concentrations if the hair care preparations act, where appropriate after dilution, for only a short time on the hair and scalp, such as, for example, shampoos or hair rinses. In these cases, for example, concentrations of about 0.2 to about 10%, preferably about 0.5 to about 3%, may be expedient.

Particular suitable hair care preparations according to the present invention are shampoo preparations comprising (i) p-hydroxylbenzylamine or a salt thereof in an amount of about 0.001 to 10 wt.-%, preferably of about 0.005 wt.-% to 5 wt.-%, more preferably of about 0.01 to 1 wt.-%, based on the total weight of the composition, (ii) water and (iii) at least one anionic surfactant. Preferably, the anionic surfactant is selected from the group consisting of sodium lauryl sulfate, ammonium lauryl sulfate, sodium lauryl ether sulfate, ammonium lauryl ether sulfate, sodium lauroyl sarconisate, sodium oleylsuccinate, ammonium lauryl sulfosuccinate, sodium dodecylbenzol sulfonate and/or triethanolamine dodecylbenzol sulfonate or mixtures thereof, such as in particular sodium lauryl sulfate, ammonium lauryl sulfate, sodium lauryl ether sulfate and/or ammonium lauryl ether sulfate. The total amount of the anionic surfactant in the compositions according to the invention ranges from 0.5 to 45 wt.-%, preferably from 1.5 to 35 wt.-%, more preferably from 7 to 25 wt.-%, in particular from 7 to 15 wt.-% based on the total weight of the composition.

Particular suitable hair conditioners according to the present invention may be rinse off or leave on conditioners, preferably rinse-off conditioners. Particular advantageous hair conditioners according to the present invention comprise (i) p-hydroxylbenzylamine or a salt thereof in an amount of about 0.001 to 10 wt.-%, preferably of about 0.005 wt.-% to 5 wt.-%, more preferably of about 0.01 to 1 wt.-%, based on the total weight of the composition, (ii) water and (iii) at least one silicone oil. In principal any silicone oil is suitable for use in the hair conditioner. However, the silicone oil is preferably selected from dimethicones, dimethiconols, polydimethylsiloxanes, arylated silicones, cyclic silicones, silicone surfactants and aminated silicones and may be volatile or non volatile. Particular suitable silicone oils are dimethicone, dimethiconol, polydimethylsiloxane which are available from various suppliers such as Dow Corning. The total amount of the at least one silicone oil in the hair conditioner is preferably selected is in the range of 0.01 to 10 wt.-%, preferably 0.02 to 7.5 wt.-%, more preferably 0.05 to 5 wt.-% and most preferably 0.1 to 3 wt.-%, based on the total weight of the composition.

In another preferred embodiment, the cosmetic compositions according to the present invention are O/W emulsions, W/O emulsions and/or gels such as shower gels or hair gels.

The O/W emulsions according to the present invention advantageously comprise (i) p-hydroxylbenzylamine or a salt thereof in an amount selected in the range of about 0.001 to 10 wt.-%, preferably of about 0.005 wt.-% to 5 wt.-%, more preferably of about 0.01 to 1 wt.-%, based on the total weight of the composition, (ii) water and (iii) at least one O/W- or Si/W-emulsifier selected from the list of glycerylstearatcitrate, glycerylstearate (self emulsifying), stearic acid, salts of stearic acid, polyglyceryl-3-methylglycosedistearate, ceteareth-20, steareth-2, steareth-12, PEG-40 stearate, phosphate esters and the salts thereof such as cetyl phosphate (Amphisol® A), diethanolamine cetyl phosphate (Amphisol® DEA), potassium cetyl phosphate (Amphisol® K), sodiumcetearylsulfat, sodium glyceryl oleate phosphate, hydrogenated vegetable glycerides phosphate, sorbitan oleate, sorbitan sesquioleate, sorbitan isostearate, sorbitan trioleate, lauryl glucoside, decyl glucoside, sodium stearoyl glutamate, sucrose polystearate and Hydrated Polyisobuten as well as mixtures thereof. Also one or more synthetic polymers may be used as an emulsifier such as for example, PVP eicosene copolymer, acrylates/C10-30 alkyl acrylate crosspolymer, acrylates/steareth-20 methacrylate copolymer, PEG-22/dodecyl glycol copolymer, PEG-45/dodecyl glycol copolymer, and mixtures thereof. In a particular preferred embodiment the O/W-emulsifier is selected from the group of cetyl phosphates such as in particular potassium cetyl phosphate (commercially available as Amphisol® K), glyceryi stearate (and) PEG 100 stearate (commercially available as Arlacel® 165) and/or polyalkylenglycolether such as in particular laureth-35 (lauryl alcohol with 35 EO units; commercially available as Brij® 35). The at least one O/W emulsifier is preferably used in an amount of about 0.001 to 10 wt.-%, more preferably in an amount of 0.1 to 7 wt.-% with respect to the total weigh of the composition. Additionally the cosmetic composition in the form of a O/W emulsion contains advantageously at least one co-emulsifier selected from the list of alkyl alcohols such as Cetyl Alcohol (Lorol C16, Lanette 16) Cetearyl Alcohol (Lanette® O), Stearyl Alcohol (Lanette® 18), Behenyl Alcohol (Lanette® 22), Glyceryl Monostearate, Glyceryl Myristate (Estol® 3650), Hydrogenated Coco-Glycerides (Lipocire Na10) without being limited to this and mixtures thereof.

The W/O emulsions according to the present invention advantageously comprise (i) p-hydroxylbenzylamine or a salt thereof in an amount selected in the range of about 0.001 to 10 wt.-%, preferably of about 0.005 wt.-% to 5 wt.-%, more preferably of about 0.01 to 1 wt.-%, based on the total weight of the composition, (ii) water and (iii) at least one W/O- or W/Si-emulsifier selected from the list of polyglyceryl-2-dipolyhydroxystearat, PEG-30 dipolyhydroxystearat, cetyl dimethicone copolyol, polyglyceryl-3 diisostearate polyglycerol esters of oleic/isostearic acid, polyglyceryl-6 hexaricinolate, polyglyceryl-4-oleate, polygylceryl-4 oleate/PEG-8 propylene glycol cocoate, magnesium stearate, sodium stearate, potassium laurate, potassium ricinoleate, sodium cocoate, sodium tallowate, potassium castorate, sodium oleate, and mixtures thereof. Further suitable W/Si-emulsifiers are Lauryl Polyglyceryl-3 Polydimethylsiloxyethyl Dimethicone and/or PEG-9 Polydimethylsiloxyethyl Dimethicone and/or Cetyl PEG/PPG-10/1 Dimethicone and/or PEG-12 Dimethicone Crosspolymer and/or PEG/PPG-18/18 Dimethicone. The at least one W/O emulsifier is preferably used in an amount of about 0.001 to 10 wt.-%, more preferably in an amount of 0.2 to 7 wt.-% with respect to the total weigh of the composition.

The gel preparations according to the present invention preferably comprise (i) p-hydroxylbenzylamine or a salt thereof in an amount selected in the range of about 0.001 to 10 wt.-%, preferably of about 0.005 wt.-% to 5 wt.-%, more preferably of about 0.01 to 1 wt.-%, based on the total weight of the composition, (ii) water and (iii) at least one water soluble thickener. Such water soluble thickeners are well known to a person skilled in the art and are e.g. listed in the "Handbook of Water soluble gums and resins" by Robert L. Davidson (Mc Graw Hill Book Company (1980)). Particularly suitable water soluble thickeners are selected from the group consisting of polyacrylic acids (e.g. commercially available under the tradename Carbomer or Carbopol®), homopolymers of 2-Acrylamido-2-methylpropansulfonic acid (e.g. commercially available as Rheothik®11-80), acrylate copolymers (e.g. commercially available under the tradename Pemulen® or Aculyn® 33), branched Poly (methacryloyloxyethyltrimethylammoniumchlorid) (INCI-name Polyquaternium-37), non-modified guar gums (e.g. commercially available under the tradename Jaguar), starch or derivatives thereof and/or hydroxyalkylcellulosen. Preferably the water soluble thickener is used in an amount of about 0.001 to 10 wt.-%, more preferably in an amount of 0.2 to 7 wt.-%, based on the total weigh of the composition.

The following examples are provided to further illustrate the compositions and effects of the present invention. These examples are illustrative only and are not intended to limit the scope of the invention in any way.

EXAMPLE 1: ANTIMICROBIAL EFFICACY

The antimicrobial activity was assessed by determination of the Minimum Inhibitory Concentration (MIC) using the agar dilution method according to DIN 58 940 at the Labor L+SAG, D–Bad Bocklet-Grossenbrach.

Culture plates with a diameter of 5.5 cm were prepared with fresh, kept liquid (50° C.) Mueller-Hinton Agar (double concentrated, Merck 1.05437)/aqua purificata comprising p-Hydroxybenzylamine (pHBA) in the concentrations indicated in Table 1 according to standard methods. After solidifying and drying (about 1 h at 36° C.), the culture plates were inoculated with 1 µl of a suspension of the respective microorganism with the colony forming unit as outlined in table 1. The inoculated plates were then incubated at 36° C. The MIC's (i.e. the concentrations where still no growth could be observed) were determined after 18 h for *E. coli, P. aeruginosa* and *S. aureus*; after 48 h for *P. acnes* and after 78 h for *A. brasiliensis* and *C. albicans*. Per sample two culture plates were prepared. As control incubated and non-incubated cultures were used. The incubated control samples showed and the non-incubated control samples did not show microbial growth.

TABLE 1

| | Test series | | | | | | | | |
|---|---|---|---|---|---|---|---|---|---|
| Sample | Final concentration in [mg/ml] | | | | | | | | |
| pHBA | 40 | 26.67 | 17.78 | 11.85 | 7.90 | 5.27 | 3.51 | 2.34 | 1.56 | 1.04 |

The suspensions of the microorganism's No. 1-4 were prepared by homogeneous suspension of 3-5 colonies of the same morphology in physiological NaCl-solution. The suspensions were adjusted such, that the haze corresponded to the Mac Farland standard 1.0 (about $3.0*10^8$ KBE*/ml). For the preparation of the suspensions of the microorganisms 5 and 6, the microorganisms have been taken with a sterile swab and diluted in an amount of physiological NaCl solution such, that the haze corresponded to the Mac Farland standard 1.0. Afterwards the suspensions of the microorganisms 1 and 3-6 have been further diluted with physiological NaCl-solution in a ratio of 1:10. The colony count was determined using a spiral plater system (see table 2).

TABLE 2

| No | Culture | | Susp. 1 | Susp. 2 |
|---|---|---|---|---|
| | | | KBE*/ml | |
| 1 | E. coli | ATCC 8739 | $2.4 * 10^7$ | $1.9 * 10^7$ |
| 2 | P. aeruginosa | ATCC 9027 | $2.7 * 10^8$ | $2.1 * 10^8$ |
| 3 | S. aureus | ATCC 6538 | $3.0 * 10^7$ | $1.8 * 10^7$ |
| 4 | P. acnes | ATCC 11828 | $2.3 * 10^7$ | $2.6 * 10^7$ |
| 5 | A. brasiliensis | ATCC 16404 | $2.9 * 10^7$ | $3.0 * 10^7$ |
| 6 | C. albicans | ATCC 10231 | $2.3 * 10^7$ | $2.0 * 10^7$ |

*Colony forming units

The results are presented in the table 3 below. As can be seen, pHBA effectively inhibits the growth of the respective microorganism.

TABLE 3

| MIC's of p-hydroxybenzylamine | |
|---|---|
| Strain | Compound pHBA MIC [mg/ml] |
| E. coli | 5.27 |
| P. acnes | 7.90 |
| P. aeruginosa | 5.27 |
| S. aureus | 5.27 |
| A. brasiliensis | 5.27 |
| C. albicans | 5.27 |

EXAMPLE 2: O/W FOUNDATION

| Ingredients | INCI | wt. % |
|---|---|---|
| Deionised Water | Aqua | Ad 100 |
| Glycerin | Glycerin | 2.00 |
| Triethanolamine | Triethanolamine | 0.80 |
| Paratexin | Methylparaben EP | 0.20 |
| Keltrol | Xanthan Gum | 0.30 |
| p-Hydroxybenzylamine | | 1.50 |
| Titanium dioxide | C.I. 77891 | 4.57 |
| SunCROMA yellow iron oxide | C.I. 77492 | 0.30 |
| SunCROMA red iron oxide | C.I. 77491 | 0.13 |
| SunCROMA black iron oxide | C.I. 77499 | 0.20 |
| DC 556 | Phenyl Trimethicone | 3.60 |
| Stearic Acid | Stearic Acid | 1.4 |
| Cetyl Alcohol | Cetyl Alcohol | 3.0 |
| Paratexin P | Propylparaben EP | 0.1 |

EXAMPLE 3: ALCOHOL FREE FACIAL TONIC

| Ingredients | INCI | wt. % |
|---|---|---|
| Polysorbate 20 | Polysorbate 20 | 2.00 |
| ALPAFLOR CALENDULA AO | Calendula Officinalis Extract, Glycerin, Water | 0.80 |
| ALPAFLOR BUDDLEJA AO | Buddleja Davidii Extract, Glycerin, Water | 0.80 |
| Arlasilk Phospholipd CDM | Sodium Coco PG-Dimonium Chloride Phosphate | 0.50 |
| Fragrance | Parfum | 0.10 |
| Deionised Water | Aqua | Ad 100 |
| Citric Acid | Citric Acid | 0.01 |
| p-Hydroxybenzylamine | | 1.00 |
| Paratexin FRP | Ethylparaben, Butylparaben, Propylparaben, Isobutylparaben | 0.10 |

EXAMPLE 4: W/O CREAM

| Ingredients | INCI | wt. % |
|---|---|---|
| Cremophor WO-7 | PEG-7 Hydrogenated Castor Oil | 2.50 |
| Elfacos ST-9 | PEG-45/Dodecyl Glycol Copolymer | 2.00 |
| Cirebelle 303 | Synthetic Wax | 5.00 |
| Cirebelle 109L | Synthetic Wax | 7.20 |
| Miglyol 818 | Caprylic/Capric/Linoleic Triglyceride | 5.00 |
| Eutanol G | Octyldodecanol | 7.50 |
| Cetiol OE | Dicaprylyl Ether | 9.20 |
| Deionised Water | Aqua | Ad 100 |
| Glycerin | Glycerin | 5.00 |
| Propylene Glycol | Propylene Glycol | 2.00 |
| Euxyl PE 9010 | Phenoxyethanol and Ethylhexylglycerin | 0.80 |
| p-Hydroxybenzylamine | | 1.50 |

EXAMPLE 5: SOOTHING GEL

| Ingredients | INCI | wt. % |
|---|---|---|
| Deionised Water | Aqua | Ad 100 |
| Keltrol CG RD | Xanthan Gum | 0.50 |
| Sodium Benzoate | Sodium Benzoate | 0.20 |
| Potassium Sorbate | Potassium Sorbate | 0.25 |

| Ingredients | INCI | wt. % |
|---|---|---|
| ALPAFLOR MARRABIUM AO | Glycerin, Aqua, Marrubium Vulgare, Sodium Benzoate, Potassium Sorbate | 3.00 |
| p-Hydroxybenzylamine | | 3.0 |

EXAMPLE 6: O/W LOTION

| Ingredients | INCI | wt. % |
|---|---|---|
| Deionised Water | Aqua | Ad 100 |
| Menthol | Menthol | 0.10 |
| Keltrol CG SFT | Xanthan Gum | 1.25 |
| Ceralution ES | Ceteareth-25, Di Sodium Ethylene Dicocamide PEG-15 Disulfate | 2.00 |
| Isofal 20 | Octyldodecanol | 5.00 |
| Paratexin EC5 | Benzoic Acid Benzyl Alcohol, Dehydroacetic Acid, Sorbic Acid | 1.00 |
| p-Hydroxybenzylamine | | 1.50 |

EXAMPLE 7: FACIAL CLEANSING GEL

| Ingredients | INCI | wt. % |
|---|---|---|
| Deionised Water | Aqua | Ad 100 |
| Carbopol AQUA SF-1 Polymer | Acrylates Copolymer | 7.50 |
| Texapon NSO-BZ | Sodium Laureth Sulfate | 41.00 |
| Miranol Ultra C 32 | Sodium Cocoamphoacetate | 5.00 |
| Hostapon CLG | Sodium Lauroyl Glutamate | 4.50 |
| Jaguar C 162 | Hydroxypropyl Guar Hydroxypropyltrimonium Chloride | 1.00 |
| p-Hydroxybenzylamine | | 0.50 |
| Euxyl K 300 | Phenoxyethanol & Methylparaben & Propylparaben & Ethylparaben & Butylparaben & Isobutylparaben | 0.80 |
| ALPAFLOR MALVA AO | Glycerin, Aqua, Malva Sylvestris (Mallow) Flower Extract, Potassium Sorbate, Sodium Benzoate | 2.00 |
| Parfum Limette | Fragrance | q.s. |
| FD&C Yellow 5 | CI 19140 | 0.50 |
| Frescolat Plus | Menthyl Lactate, Menthol | 0.20 |
| Dehyton AB-30 | Coco Betaine | 2.00 |
| Rewoderm LI S 80 | PEG-200 Hydrogenated Glyceryl Palmate & PEG-7 Glyceryl Cocoate | 1.00 |
| Citric Acid | Citric Acid | q.s. |

EXAMPLE 8: LEAVE-ON HAIR AND SCALP CONDITIONER

| Ingredients | INCI | wt. % |
|---|---|---|
| Deionised Water | Aqua | Ad 100 |
| Ethanol DEB 96 | Alcohol denat. | 30.00 |
| PVP/VA Copolymer | PVP/VA Copolymer | 2.50 |
| Euxyl K-300 | Phenoxyethanol, Methylparaben, Butylparaben, Ethylparaben, Propylparaben, Isobutylparaben | 0.80 |
| Protachem HCO-40 | PEG-40 Hydrogenated Castor Oil | 0.50 |
| Fragrance ADAM | Parfum | 0.10 |
| Triethanolamine 99% | Triethanolamine | 0.01 |
| FD & C Yellow No 5 (0.5% Solution) | CI 19140, Aqua | 0.10 |
| FD & C Blue No 1 (0.5% Solution) | CI 42090, Aqua | 0.10 |
| p-Hydroxybenzylamine | | 0.5 |

EXAMPLE 9: ANTI DANDRUFF SHAMPOO

| INCI Nomenclature | wt. % |
|---|---|
| Aqua (water) | Ad 100 |
| Ammonium laureth sulfate | 10.00 |
| Ammonium lauryl sulfate | 5.00 |
| Glycol distearate | 1.00 |
| Dimethicone | 1.00 |
| Cetyl alcohol | 0.50 |
| Cocamide MEA | 3.00 |
| p-Hydroxybenzylamine | 2.50 |
| ZPT | 0.50 |
| Guar hydroxypropyltrimonium chloride | 0.20 |
| Hydrogenated polydecene | 1.00 |
| Polyquaternium 10 | 0.30 |
| PEG 7m | 0.50 |
| Trimethylpropane tricaprylate/tricaprate | 1.00 |
| Preservative | q.s. |
| Fragrance | 0.30 |
| E 104, E 110, E 132 | 0.02 |

EXAMPLE 10: CLEAR ANTI DANDRUFF SHAMPOO WITH PLANT EXTRACTS

| INCI Nomenclature | wt. % |
|---|---|
| Aqua (water) | Ad 100 |
| Sodium laureth sulfate | 10.00 |
| Lauryl glucoside | 6.00 |
| Cocamidopropyl betaine, | 2.00 |
| Propylene glycol | 2.00 |
| Perfume oil | 1.25 |
| Sodium citrate | 0.25 |
| Sodium benzoate | 0.20 |
| Panthenol | 1.00 |
| Sodium formate | 0.20 |
| Polyquaternium-10 | 0.20 |
| Hydroxypropyl guar hydroxypropyltrimonium chloride | 0.05 |
| p-Hydroxybenzylamine | 5.00 |
| PEG-35 castor oil | 1.00 |
| Maris sal | 1.25 |
| Polysorbate 20 | 1.00 |
| Tocopheryl acetate | 0.20 |
| Prunus armeniaca | 0.20 |
| Echinacea purpurea | 0.05 |
| Retinyl palmitate | 0.05 |
| Tocopherol | 0.05 |
| Linoleic acid | 0.20 |
| Preservative | 1.00 |
| CI77891 | 0.02 |

EXAMPLE 11: RINSE-OFF HAIR AND SCALP CONDITIONER

| INCI Nomenclature | wt. % |
| --- | --- |
| Aqua (water) | Ad 100 |
| Stearyl alcohol | 2.50 |
| Cetyl alcohol | 2.50 |
| Behentrimonium chloride | 1.30 |
| Dimethicone | 2.00 |
| p-Hydroxybenzylamine | 1.50 |
| Fragrance | 0.50 |
| Butylene glycol | 2.00 |
| Methyl parabene | 0.30 |

The invention claimed is:

1. A cosmetic composition for topical application comprising:
   (i) a cosmetically acceptable carrier,
   (ii) at least one cosmetic agent selected from the group consisting of surfactants, emulsifiers, thickeners, and oils, and
   (iii) 0.001 to 10 wt.-%, based on the total weight of the composition, of a hydrochloride salt of p-hydroxybenzylamine as an antimicrobial agent.

2. The composition according to claim 1, wherein the antimicrobial agent is present in an amount of 0.005 to 5 wt. %, based on the total weight of the composition.

3. The composition according to claim 1, wherein the antimicrobial agent is present in an amount of 0.01 to 1 wt. %, based on the total weight of the composition.

4. The composition according to claim 1, wherein the composition is a shampoo preparation, a hair conditioner, an O/W emulsion, a W/O emulsion or a gel.

5. The composition according to claim 1, wherein the composition is a topical composition to be applied to human skin, scalp and/or hair.

6. A method of treating scalp, wherein the method comprises contacting the scalp with a rinse-off composition in the form of a shampoo or a conditioner comprising the cosmetic composition according to claim 1, and thereafter rinsing the scalp with water.

* * * * *